(12) United States Patent
Vela Avitúa et al.

(10) Patent No.: US 12,344,903 B2
(45) Date of Patent: Jul. 1, 2025

(54) METHOD FOR PREDICTING SURVIVAL FOLLOWING *Streptococcus iniae* INFECTION

(71) Applicants: BENCHMARK GENETICS LIMITED, Sheffield (GB); BENCHMARK GENETICS NORWAY AS, Bergen (NO)

(72) Inventors: Sergio Vela Avitúa, Vinterbro (NO); Carlos Lozano, Ås (NO); Morten Rye, Grøa (NO)

(73) Assignees: BENCHMARK GENETICS LIMITED, Sheffield (GB); BENCHMARK GENETICS NORWAY AS, Bergen (NO)

( * ) Notice: Subject to any disclaimer, the term of this patent is extended or adjusted under 35 U.S.C. 154(b) by 767 days.

(21) Appl. No.: 17/618,041

(22) PCT Filed: Jun. 9, 2020

(86) PCT No.: PCT/GB2020/051394
§ 371 (c)(1),
(2) Date: Dec. 10, 2021

(87) PCT Pub. No.: WO2020/249939
PCT Pub. Date: Dec. 17, 2020

(65) Prior Publication Data
US 2022/0307092 A1  Sep. 29, 2022

(30) Foreign Application Priority Data

Jun. 10, 2019 (GB) ........................... 1908261

(51) Int. Cl.
*C12Q 1/6883* (2018.01)
*C12Q 1/6888* (2018.01)

(52) U.S. Cl.
CPC ...... *C12Q 1/6888* (2013.01); *C12Q 2600/118* (2013.01); *C12Q 2600/124* (2013.01); *C12Q 2600/156* (2013.01)

(58) Field of Classification Search
CPC ............ C12Q 1/6888; C12Q 2600/118; C12Q 2600/124; C12Q 2600/156
See application file for complete search history.

(56) References Cited

FOREIGN PATENT DOCUMENTS

CN        103642802 A1 * 12/2013 ............. C12N 15/11

OTHER PUBLICATIONS

Webster, Carl D., and Chhorn Lim, eds. Tilapia: biology, culture, and nutrition. CRC Press, 2006. (Year: 2006).*

(Continued)

*Primary Examiner* — Evelyn Y Pyla
*Assistant Examiner* — Jagamya Vijayaraghavan
(74) *Attorney, Agent, or Firm* — Sheridan Ross P.C.

(57) ABSTRACT

Methods of predicting survival following *Streptococcus iniae* infection in tilapia, the method comprising determining the alleles present at one or more, optionally two or more, DNA polymorphism in the tilapia and predicting whether or not the tilapia will survive *Streptococcus iniae* infection based on the determination of the alleles, methods of detecting in a sample from a tilapia the presence or absence of the alleles present at one or more, optionally two or more, DNA polymorphism associated with survival following *Streptococcus iniae* infection, relating methods of obtaining an indication of risk of a tilapia becoming infected by *Streptococcus iniae* comprising, methods of producing broodstock, offspring or eggs using so selected tilapia, all optionally using DNA polymorphisms located on linkage group 8 of the tilapia genome.

7 Claims, 6 Drawing Sheets
Specification includes a Sequence Listing.

(56) References Cited

OTHER PUBLICATIONS

Broodstock. (n.d.). U.S. Fish & Wildlife Service. Retrieved Sep. 20, 2024, from https://www.fws.gov/glossary/broodstock.*

Examining fingerlings. (n.d.). U.S. Fish & Wildlife Service. Retrieved Sep. 20, 2024, from https://www.fws.gov/media/examining-fingerlings.*

Translation of CN103642802.*

Agnew et al. "*Streptococcus iniae:* An aquatic pathogen of global veterinary significance and a challenging candidate for reliable vaccination," Veterinary Microbiology, Apr. 2007, vol. 122, No. 1-2, pp. 1-15.

Gao et al. "MHC Class IIB gene polymorphisms associated with resistance/susceptibility to *Streptococcus agalactiae* in Nile tilapia Oreochromis niloticus," Diseases of Aquatic Organisms, Apr. 2019, vol. 133, No. 3, pp. 253-261.

Shoemaker et al. "Additive genetic variation in resistance of Nile tilapia (Oreochromis niloticus) to *Streptococcus iniae* and *S. agalactiae* capsular type Ib: Is genetic resistance correlated?" Aquaculture, Oct. 2016, vol. 468, pp. 193-198.

Vela Avitúa et al. "Genome-wide association study for survival to *Streptococcus iniae* and *S. agalactiae* in Nile Tilapia (Oreochromis niloticus)," XII Simposio Internacional de Aquicultura, Nov. 22, 2018, [retrieved online from: abccam.com.br/wp-content/uploads/2018/11/12-Genome-wide-association-study-for-survival-to-Streptococcus-iniae-and-S.-agalactiae-in-Nile-Tilapia-Oreochromis-niloticus-Sergio-Vela.pdf].

Wenne "Single nucleotide polymorphism markers with applications in aquaculture and assessment of its impact on natural populations," Aquatic Living Resources, Nov. 2017, vol. 31, article 2, 17 pages.

International Search Report and Written Opinion for International (PCT) Patent Application No. PCT/GB2020/051394, dated Sep. 11, 2020, 8 pages.

\* cited by examiner

SEQUENCE LISTING

```
<160> NUMBER OF SEQ ID NOS: 20

<210> SEQ ID NO 1
<211> LENGTH: 201
<212> TYPE: DNA
<213> ORGANISM: Oreochromis niloticus
<220> FEATURE:
<223> OTHER INFORMATION: NC_031973.1_7142946 increased survival allele

<400> SEQUENCE: 1
agcaaatcgc atgtgtgagc cagcccgaag tcacaggagc tgtccttggt gctgagaggg      60
aggcagctgt ycgagtgttt tcctgaacag acctgaagcc cgctggaytt tgtttctttc     120
cttcagctaa tcctttccat gcagcctgca tcaggatgtc aattcataat aaaaagtata     180
caggcaccaa gcagtcaatc a                                                201

<210> SEQ ID NO 2
<211> LENGTH: 201
<212> TYPE: DNA
<213> ORGANISM: Oreochromis niloticus
<220> FEATURE:
<223> OTHER INFORMATION: NC_031973.1_7142946 decreased survival allele

<400> SEQUENCE: 2
agcaaatcgc atgtgtgagc cagcccgaag tcacaggagc tgtccttggt gctgagaggg      60
aggcagctgt ycgagtgttt tcctgaacag acctgaagcc tgctggaytt tgtttctttc     120
cttcagctaa tcctttccat gcagcctgca tcaggatgtc aattcataat aaaaagtata     180
caggcaccaa gcagtcaatc a                                                201

<210> SEQ ID NO 3
<211> LENGTH: 201
<212> TYPE: DNA
<213> ORGANISM: Oreochromis niloticus
```

<220> FEATURE:
<223> OTHER INFORMATION: NC_031973.1_7775443 increased survival allele

<400> SEQUENCE: 3
tgtctgacag tccttattca gcactgatga tggaggccta ycagaggcca gcatttcggg    60
ctcctgctaa cattacaaaa taaaatacca gctcgtatgt ttgacttact gaaacctgca   120
tgtcctctca cggcycagtg ctggtcggca gcgccygggg gtgaagcgat gtcacgacyc   180
ygtgcacgtt tacatcatcg t                                             201

<210> SEQ ID NO 4
<211> LENGTH: 201
<212> TYPE: DNA
<213> ORGANISM: Oreochromis niloticus
<220> FEATURE:
<223> OTHER INFORMATION: NC_031973.1_7775443 decreased survival allele

<400> SEQUENCE: 4
tgtctgacag tccttattca gcactgatga tggaggccta ycagaggcca gcatttcggg    60
ctcctgctaa cattacaaaa taaaatacca gctcgtatgt atgacttact gaaacctgca   120
tgtcctctca cggcycagtg ctggtcggca gcgccygggg gtgaagcgat gtcacgacyc   180
ygtgcacgtt tacatcatcg t                                             201

<210> SEQ ID NO 5
<211> LENGTH: 201
<212> TYPE: DNA
<213> ORGANISM: Oreochromis niloticus
<220> FEATURE:
<223> OTHER INFORMATION: NC_031973.1_6323968 increased survival allele

<400> SEQUENCE: 5 tttttgctc tgtgtggtgg ttttatggct tcttcacact aacatggttc ttatgtaaat    60
agttcctgag atgttygtcc tggaggagca gcacagtgca aatctccacg ctgtaagcct   120
gaacaaactg atgcttgttc agcccttga tgctgaaggc aaattaaaga gcgctggctc    180
tccacgcytc ctctggtata a                                             201

<210> SEQ ID NO 6
<211> LENGTH: 201
<212> TYPE: DNA
<213> ORGANISM: Oreochromis niloticus
<220> FEATURE:
<223> OTHER INFORMATION: NC_031973.1_6323968 decreased survival allele

<400> SEQUENCE: 6 tttttgctc tgtgtggtgg ttttatggct tcttcacact aacatggttc ttatgtaaat    60
agttcctgag atgttygtcc tggaggagca gcacagtgca gatctccacg ctgtaagcct   120
gaacaaactg atgcttgttc agcccttga tgctgaaggc aaattaaaga gcgctggctc    180
tccacgcytc ctctggtata a                                             201

<210> SEQ ID NO 7
<211> LENGTH: 201
<212> TYPE: DNA
<213> ORGANISM: Oreochromis niloticus
<220> FEATURE:
<223> OTHER INFORMATION: NC_031973.1_7142916 increased survival allele

<400> SEQUENCE: 7
cactctggtg gatgttgaga agctaatgtg agcaaatcgc atgtgtgagc cagcccgaag    60

```
tcacaggagc tgtccttggt gctgagaggg aggcagctgt acgagtgttt tcctgaacag    120
acctgaagcc ygctggaytt tgtttctttc cttcagctaa tcctttccat gcagcctgca    180
tcaggatgtc aattcataat a                                              201
```

<210> SEQ ID NO 8
<211> LENGTH: 201
<212> TYPE: DNA
<213> ORGANISM: Oreochromis niloticus
<220> FEATURE:
<223> OTHER INFORMATION: NC_031973.1_7142916 decreased survival allele

<400> SEQUENCE: 8

```
cactctggtg gatgttgaga agctaatgtg agcaaatcgc atgtgtgagc cagcccgaag    60
tcacaggagc tgtccttggt gctgagaggg aggcagctgt gcgagtgttt tcctgaacag    120
acctgaagcc ygctggaytt tgtttctttc cttcagctaa tcctttccat gcagcctgca    180
tcaggatgtc aattcataat a                                              201
```

<210> SEQ ID NO 9
<211> LENGTH: 201
<212> TYPE: DNA
<213> ORGANISM: Oreochromis niloticus
<220> FEATURE:
<223> OTHER INFORMATION: NC_031973.1_7497722 increased survival allele

<400> SEQUENCE: 9

```
gcatatgcag aatyaaagaa ccatygagct gtgatttgac aaaggaagct gcgagagtgt    60
gcagcgcttt cattgaaaag ctaaaacaca aaatccattt tatggggtta aaaatgggat    120
tgggcaggtg ggygactcac ctgtcttctt ggtggaaagc ctataagatc agctgacctg    180
ctcattgctg tgtctctgac g                                              201
```

<210> SEQ ID NO 10
<211> LENGTH: 201
<212> TYPE: DNA
<213> ORGANISM: Oreochromis niloticus
<220> FEATURE:
<223> OTHER INFORMATION: NC_031973.1_7497722 decreased survival allele

<400> SEQUENCE: 10

```
gcatatgcag aatyaaagaa ccatygagct gtgatttgac aaaggaagct gcgagagtgt    60
gcagcgcttt cattgaaaag ctaaaacaca aaatccattt catggggtta aaaatgggat    120
tgggcaggtg ggygactcac ctgtcttctt ggtggaaagc ctataagatc agctgacctg    180
ctcattgctg tgtctctgac g                                              201
```

<210> SEQ ID NO 11
<211> LENGTH: 201
<212> TYPE: DNA
<213> ORGANISM: Oreochromis niloticus
<220> FEATURE:
<223> OTHER INFORMATION: NC_031973.1_9167743 increased survival allele

<400> SEQUENCE: 11

```
gctctggaaa gtgacttaac atcagagtgt gctgatccytg tgtgcgtttg tgtaaactgt   60
gggagcagga agcagtcagc acctcttcaa agtaagagtc tagtgtttgc gctgctctga   120
ttttagcggc tggactggaa gaatcgtccc gtctgcacgg gttgaccttc tgtgatctgt   180
gatcagaact tcggagttac t                                              201
```

```
<210> SEQ ID NO 12
<211> LENGTH: 201
<212> TYPE: DNA
<213> ORGANISM: Oreochromis niloticus
<220> FEATURE:
<223> OTHER INFORMATION: NC_031973.1_9167743 decreased survival allele

<400> SEQUENCE: 12
gctctggaaa gtgacttaac atcagagtgt gctgatcytg tgtgcgtttg tgtaaactgt      60
gggagcagga agcagtcagc acctcttcaa agtaagagtc cagtgtttgc gctgctctga     120
ttttagcggc tggactggaa gaatcgtccc gtctgcacgg gttgaccttc tgtgatctgt     180
gatcagaact tcggagttac t                                               201

<210> SEQ ID NO 13
<211> LENGTH: 201
<212> TYPE: DNA
<213> ORGANISM: Oreochromis niloticus
<220> FEATURE:
<223> OTHER INFORMATION: NC_031973.1_7782524 increased survival allele

<400> SEQUENCE: 13 cccttttaa tgcctcactt ttctctgatt gycctcctct gacayacaga aggtttcagc       60
agcagctggc tgtagtttct cygctcacac ctgagctttg cggtcagatg accaygtcag    120
ggtytctcyg tgacatcaca catatccgtg tctgtgctgc cctggagatc tgccgtacct    180
gatgatggga acctctaaga a                                              201

<210> SEQ ID NO 14
<211> LENGTH: 201
<212> TYPE: DNA
<213> ORGANISM: Oreochromis niloticus
<220> FEATURE:
<223> OTHER INFORMATION: NC_031973.1_7782524 decreased survival allele

<400> SEQUENCE: 14 cccttttaa tgcctcactt ttctctgatt gycctcctct gacayacaga aggtttcagc       60
agcagctggc tgtagtttct cygctcacac ctgagctttg tggtcagatg accaygtcag    120
ggtytctcyg tgacatcaca catatccgtg tctgtgctgc cctggagatc tgccgtacct    180
gatgatggga acctctaaga a                                              201

<210> SEQ ID NO 15
<211> LENGTH: 201
<212> TYPE: DNA
<213> ORGANISM: Oreochromis niloticus
<220> FEATURE:
<223> OTHER INFORMATION: NC_031973.1_9209387 increased survival allele

<400> SEQUENCE: 15
agacattccc tacagatctg caaacttgga ttacttcgag tattcatcag tcgcccaaca      60
acagaaactg aatagaaaac agctggaaca cctggatgta ggagtgctgt gacacaactt    120
cagattttaa ctgtgagctc agtttactga attactgaac aacttataca tcatcctcat    180
caccaccatc atcatcatcc t                                              201

<210> SEQ ID NO 16
<211> LENGTH: 201
<212> TYPE: DNA
<213> ORGANISM: Oreochromis niloticus
<220> FEATURE:
<223> OTHER INFORMATION: NC_031973.1_9209387 decreased survival allele
```

<400> SEQUENCE: 16
agacattccc tacagatctg caaacttgga ttacttcgag tattcatcag tcgcccaaca      60
acagaaactg aatagaaaac agctggaaca cctggatgta agagtgctgt gacacaactt     120
cagattttaa ctgtgagctc agttactga attactgaac aacttataca tcatcctcat     180
caccaccatc atcatcatcc t                                               201

<210> SEQ ID NO 17
<211> LENGTH: 201
<212> TYPE: DNA
<213> ORGANISM: Oreochromis niloticus
<220> FEATURE:
<223> OTHER INFORMATION: NC_031973.1_9485417 increased survival allele

<400> SEQUENCE: 17
aatgcacytg acctctgaac actcacagaa atctaaaaac gagycatctg atgtaaactg      60
acctgaagac tgaagagaag aagacaggag gaagtaaagc tgtyaagaag cagtgcctgc     120
agctggagca ccaccaccay ccacacycac tgccatggaa acaaccgcgg gtagtttcca     180
tggcagagtg tcactgacta t                                               201

<210> SEQ ID NO 18
<211> LENGTH: 201
<212> TYPE: DNA
<213> ORGANISM: Oreochromis niloticus
<220> FEATURE:
<223> OTHER INFORMATION: NC_031973.1_9485417 decreased survival allele

<400> SEQUENCE: 18
aatgcacytg acctctgaac actcacagaa atctaaaaac gagycatctg atgtaaactg      60
acctgaagac tgaagagaag aagacaggag gaagtaaagc cgtyaagaag cagtgcctgc     120
agctggagca ccaccaccay ccacacycac tgccatggaa acaaccgcgg gtagtttcca     180
tggcagagtg tcactgacta t                                               201

<210> SEQ ID NO 19
<211> LENGTH: 201
<212> TYPE: DNA
<213> ORGANISM: Oreochromis niloticus
<220> FEATURE:
<223> OTHER INFORMATION: NC_031973.1_5545222 increased survival allele

<400> SEQUENCE: 19
tatcggtctc atccagcctg ggactgggtt aggtcaccta gaaggaactg gaaagaacca      60
ctactctgct tagcctgctg ccaccacaac ccaaccgcag agggaacatg gtgatgctct     120
tatttctccc ttctgttatt ctcagaggga accactcaca ctttctgctg ctggcagaca     180
tctgctcatc actgggctga a                                               201

<210> SEQ ID NO 20
<211> LENGTH: 201
<212> TYPE: DNA
<213> ORGANISM: Oreochromis niloticus
<220> FEATURE:
<223> OTHER INFORMATION: NC_031973.1_5545222 decreased survival allele

<400> SEQUENCE: 20
tatcggtctc atccagcctg ggactgggtt aggtcaccta gaaggaactg gaaagaacca      60
ctactctgct tagcctgctg ccaccacaac ccaaccgcag cgggaacatg gtgatgctct     120

```
tatttctccc ttctgttatt ctcagaggga accactcaca ctttctgctg ctggcagaca      180
tctgctcatc actgggctga a                                                201
```

METHOD FOR PREDICTING SURVIVAL FOLLOWING *Streptococcus iniae* INFECTION

CROSS REFERENCE TO RELATED APPLICATIONS

This application is a national stage application under 35 U.S.C. 371 and claims the benefit of PCT Application No. PCT/GB2020/051394 having an international filing date of 9 Jun. 2020, which designated the United States, and which PCT application claimed the benefit of Great Britain Patent Application No. 1908261.9 filed 10 Jun. 2019, the contents of each of which are incorporated herein by reference in their entireties.

REFERENCE TO SEQUENCE LISTING

This application contains a Sequence Listing submitted as an electronic text file named "P132119WO_sequence_listing_9jun.2020.txt", having a size in bytes of 9,000 bytes, and created on 9 Jun. 2020. The information contained in this electronic file is hereby incorporated by reference in its entirety pursuant to 37 CFR § 1.52 (e) (5).

The present invention relates to methods for predicting survival following *Streptococcus iniae* infection in tilapia, especially Nile tilapia, more specifically to predicting such survival by the analysis of DNA polymorphisms, and the use of DNA polymorphisms for detecting tilapia that are more likely to survive *Streptococcus iniae* infection.

*Streptococcus iniae* (*S. iniae*) is a species of bacterium that has emerged as a problematic fish pathogen in aquaculture operations worldwide. *S. iniae* is highly pathogenic in many species of freshwater, marine, and euryhaline fish, and outbreaks may be associated with significant levels of mortality. It is, therefore, one of the foremost economically important pathogens in intensive aquaculture. In 1997, the global economic impact of *S. iniae* infection to the aquaculture industry was estimated at US$100 million.

Tilapia is the common name for a number of species of tilapiine cichlid fish that includes Nile tilapia (*Oreochromis niloticus*). Tilapia are important in artisanal fishing in Africa, and they are used in aquaculture and aquaponics. Millions of tonnes of tilapia are farmed annually. Nile tilapia can live longer than 10 years and reach a weight exceeding 5 kg. It has been cultured for thousands of years, and it remains the predominant culture of tilapia worldwide.

Tilapia are susceptible to *S. iniae* infection. The symptoms exhibited by tilapia include being lethargic, erratic swimming, dark skin pigmentation, exophthalmia with opacity and haemorrhage in eye, abdominal distension, diffused haemorrhaging in operculum, around mouth, anus and base of fins, enlarged, nearly black spleen, and high mortality.

Measures to try to control *S. iniae* infection in fish include limiting feeding, reducing fish stock density, lowering water temperature, application of probiotics, use of chemical agents such as antibiotics and vaccination. All of these measure are associated with limited success and/or with imposition of unfavourable culturing conditions.

There is, therefore, a need for effective means for reducing *S. iniae* infection in tilapia in a manner that permits favourable or at least normal culturing conditions.

Accordingly, an aspect of the invention provides a method of predicting survival following *Streptococcus iniae* infection in tilapia, the method comprising determining the alleles present at one or more DNA polymorphism in the tilapia and predicting whether or not the tilapia is will survive *Streptococcus iniae* infection based on the determination of the alleles.

Another aspect of the invention provides a method of detecting in a sample from a tilapia the presence or absence of the alleles present at one or more DNA polymorphism associated with survival following *Streptococcus iniae* infection. In embodiments of the invention, the alleles are indicative of the tilapia surviving *Streptococcus iniae* infection. In further embodiments, the alleles are indicative of the tilapia dying following *Streptococcus iniae* infection. In yet further embodiments in which more than one allele is determined, the alleles are indicative of the tilapia having an increased or decreased chance of survival following *Streptococcus iniae* infection.

Another aspect of the invention provides a method of obtaining an indication of risk of a tilapia becoming infected by *Streptococcus iniae* comprising a method according to the invention.

Another aspect of the invention provides use of one or more DNA polymorphism associated with survival following *Streptococcus iniae* infection for detecting tilapia that are more or less likely to survive following *Streptococcus iniae* infection.

Accordingly, by selecting fish that are more likely to survive following *S. iniae* infection, there is no or less need to avoid or minimise infection by culturing fish under conditions that are unfavourable to *S. iniae* and so unfavourable to the growth and survival of the tilapia themselves. There is also no or less need to use expensive and/or contaminating chemical agents and no or less need to vaccinate the fish against *S. iniae* infection. Instead, the fish can be cultured under conditions that are commercially most favourable.

In embodiments of the invention, the one or more DNA polymorphism is located on linkage group 8 of the tilapia genome.

For all aspects of the invention, the alleles may be determined/detected using any known method, for example by nucleotide sequencing. Suitable methods include genotyping, such as by double digest restriction-site associated DNA sequencing (ddRADseq), genotyping by sequencing and real time PCR.

The DNA polymorphisms of the present invention have two alleles. One allele is predictive of survival following *Streptococcus iniae* infection (the survival allele), and the other allele is predictive of death following *Streptococcus iniae* infection (the non-survival allele). Each diploid tilapia has two copies of the one or more polymorphism of the present invention (one copy per set of chromosomes). The step of determining/detected the alleles in the present invention therefore includes the step of analysing the one or more DNA polymorphism in each set of chromosomes in order to determine whether each copy of the DNA polymorphism present is a survival allele or is a non-survival allele.

When a tilapia subjected to the method of the present invention is determined to be homozygous for the survival allele for the DNA polymorphism, the tilapia is predicted to survive following *Streptococcus iniae* infection.

By contrast, when a tilapia subjected to the method of the present invention is determined to homozygous for the non-survival allele for the DNA polymorphism, the tilapia is predicted to die following *Streptococcus iniae* infection.

When a tilapia subjected to the method of the present invention is determined to have one copy of the survival allele for the DNA polymorphism and one copy of the non-survival allele for the DNA polymorphism, the tilapia would not be predicted according to the present invention to be to survive following *Streptococcus iniae* infection. It may, however, have a level of survivability following *Streptococcus iniae* infection that is between that of tilapia that are homozygotic for the survival allele and tilapia that are homozygotic for the non-survival allele.

The one or more DNA polymorphism may one of the DNA polymorphism discovered in the quantitative trait locus (QTL) at linkage group 8 in Nile tilapia (see e.g. FIGS. 3 and 4), or at an orthologous chromosome in another tilapia. The DNA polymorphisms are linked by locus in the tilapia genome and by their ability to predict survival following *Streptococcus iniae* infection. The linkage group may be that defined by the sequence with GenBank accession no. NC_031973.1.

The DNA polymorphism may be a single nucleotide polymorphism (SNP), a multiple nucleotide polymorphism, an addition mutation, or a deletion mutation. Each type of DNA polymorphism provided above is contemplated individually as part of the present invention for the step of determining/detecting in the methods of the present invention.

In embodiments of the invention, the one or more DNA polymorphism is selected from the group consisting of: NC_031973.1_7142946; NC_031973.1_9167743; NC_031973.1_6323968; NC_031973.1_7142916; NC_031973.1_7497722; NC_031973.1_7775443; NC_031973.1_7782524; NC_031973.1_9209387; NC_031973.1_9485417; and NC_031973.1_5545222.

Each of the above DNA polymorphisms is contemplated individually as part of the present invention. Any one or combination of the aforementioned DNA polymorphisms may be extracted from the lists and used in the present invention. The methods of the present invention may involve the determination of alleles present in any one or more of the polymorphism described above, in addition to any further polymorphisms that are predictive for survival or death following *Streptococcus iniae* infection.

Combinations of two or more DNA polymorphisms form a characteristic haplotype in which each individual DNA polymorphism that is predictive of survival contributes to the overall probability of the tilapia survival. In this manner, the predictive power of the methods is enhanced by including increasing numbers of DNA polymorphisms in the haplotype.

In embodiments of the invention, the method comprises determining the alleles present at two or more DNA polymorphism in the tilapia, preferably determining the alleles present at NC_031973.1_9209387 and NC_031973.1_9485417.

The methods of the invention may be applied to any tilapia species. In a preferred embodiment, the tilapia is Nile tilapia.

The analysis of alleles may be carried out on any suitable tissue sample from the tilapia. Such samples suitable for extraction and analysis of alleles include fin sampled, such as pelvic fin sampled. The sampling method may be selected to minimise the distress and/or damage to the tilapia so as to not significantly affect the subsequent behaviour, breeding outcomes and/or egg production of the tilapia.

A tilapia that is predicted to survive following *Streptococcus iniae* infection, or to have detected alleles that indicate survival following *Streptococcus iniae* infection, according to methods of the present invention, is likely to produce offspring that will survive following *Streptococcus iniae* infection.

Accordingly, an aspect of the present invention provides a method of producing broodstock, comprising: (i) selecting a tilapia that is predicted to survive following *Streptococcus iniae* infection by a method comprising the method according to the invention; and (ii) using the tilapia to form the broodstock. An aspect of the invention provides the broodstock produced according to this method.

Conversely, a tilapia that is predicted to die following *Streptococcus iniae* infection, or to have detected alleles that indicate death following *Streptococcus iniae* infection, according to methods of the present invention, is likely to produce offspring that will die following *Streptococcus iniae* infection. Such tilapia would excluded as broodstock.

A further aspect of the present invention provides a method of producing tilapia offspring, comprising: (i) selecting a tilapia that is predicted to survive following *Streptococcus iniae* infection by a method comprising the method according to the invention; and (ii) using the tilapia to produce offspring. An aspect of the invention provides the offspring produced according to this method.

A tilapia that is predicted to have to survive following *Streptococcus iniae* infection, or to have detected alleles that indicate survival following *Streptococcus iniae* infection, according to methods of the present invention, is likely to produce eggs the fertilisation of which produces offspring that will survive following *Streptococcus iniae* infection.

Accordingly, an aspect of the invention provides a method of producing tilapia eggs, comprising: (i) selecting a tilapia that is predicted to survive following *Streptococcus iniae* infection by a method comprising the method according to the invention; and (ii) using the tilapia to produce the eggs. An aspect of the invention provides the eggs produced according to this method.

The polymorphisms, including selections and combinations thereof, as discussed above may be those referred to in any of the aspects of the present invention.

The present invention also relates to an isolated polynucleotide comprising one or more of the DNA polymorphisms selected from the group provided above and located within a portion of the tilapia genome. Exemplary sequences for such isolated polynucleotides may be found in Tables 1-3.

*Streptococcus iniae* infection of tilapia is a widely-described infection, which may be tested for by any suitable methods known to the skilled person.

The present invention is described by way of example with reference to the accompanying drawings in which.

EXAMPLE 1—IDENTIFYING SNPS THAT PREDICT SURVIVAL FOLLOWING *STREPTOCOCCUS INIAE* INFECTION

Nile tilapia (*Oreochromis niloticus*) were used in a genome-wide association study for survival following *Strep-* tococcus iniae infection. A total of 144 full sib families were produced using 72 sires and 144 dams. Families were produced by natural mating in single pair breeding units. A hierarchical nested design was used where each male was mated with two different females.

Families were reared in separate units until the fish grew large enough to tag—i.e. reached their tagging size. On average 61 days after egg collection, fish from all families were Passive Integrated Transponder (PIT)-tagged and representatives from all families were stocked in two holding tanks. At the time of tagging, tissue samples from the pelvic fin of individual fish were obtained, and stored in ethanol 97% in separate 1.5 ml Eppendorf tubes with individual identification. After collection, samples were kept at −20° C. and sent for analysis.

Streptococcus iniae Challenge Test

Fish were placed in eight acclimation units. A total of 2686 fish having an average weight of around 30 g were individually injected with S. iniae and PIT-tag registered. Fish were then stocked together in a large tank. Mortality was recorded daily during acclimation and after injection, registering PIT tag and date of mortality for each fish.

Figure 1:
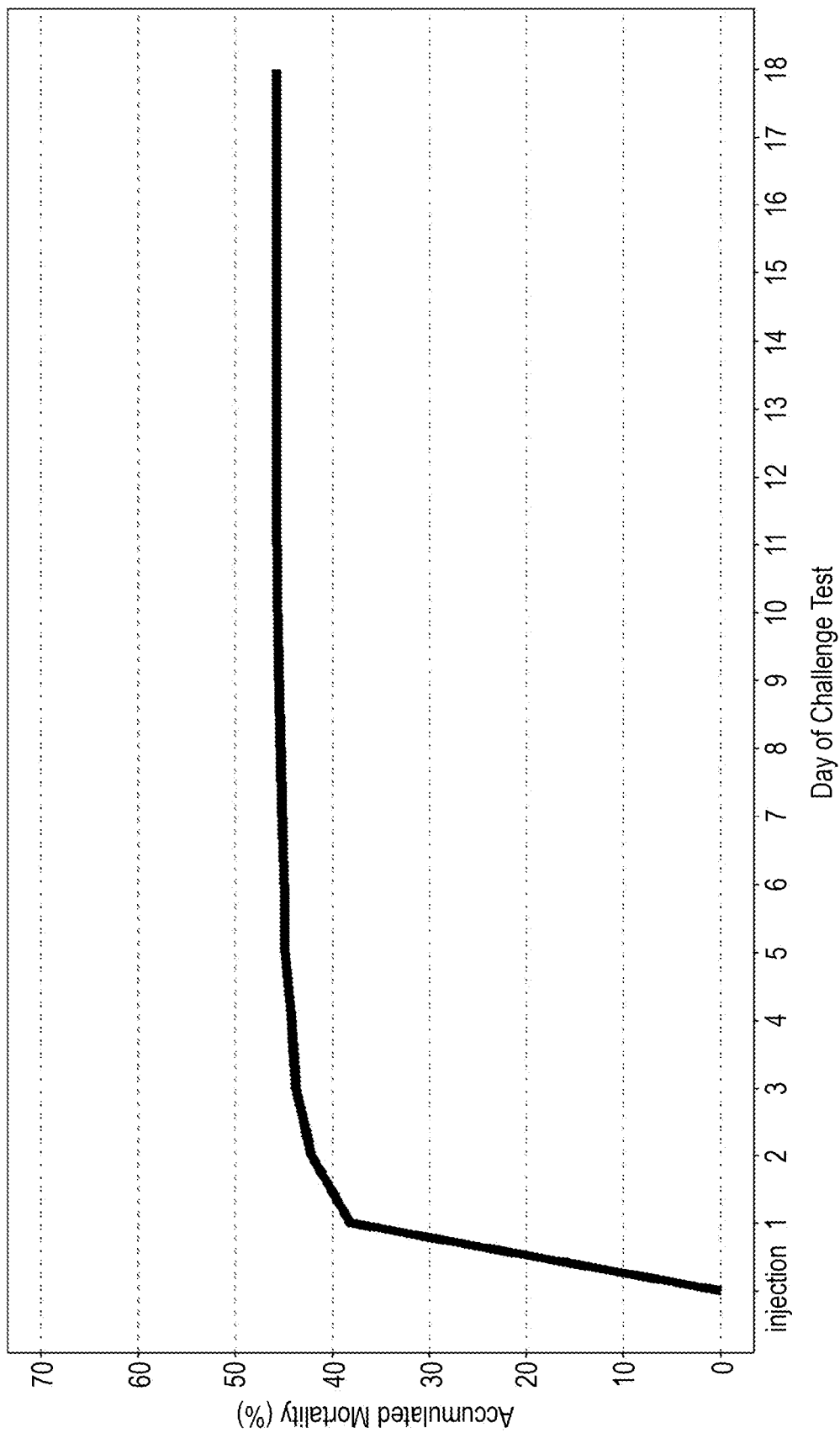
FIG. 1 shows the accumulated mortality over 21 days of a *S. iniae* challenge test.

Most of the fish died on the first and second day after injection, and after day 5 daily mortalities were below 1% daily and after day 12 practically no further mortalities occurred (FIG. 1). The test was terminated after 21 days. Accumulated mortality at the end of test was 46%.

Brain tissue samples were collected from 265 fish that died during the trial, and 99% of these samples yielded pure cultures of S. iniae suggesting the bacteria became systemic.

Figure 2:
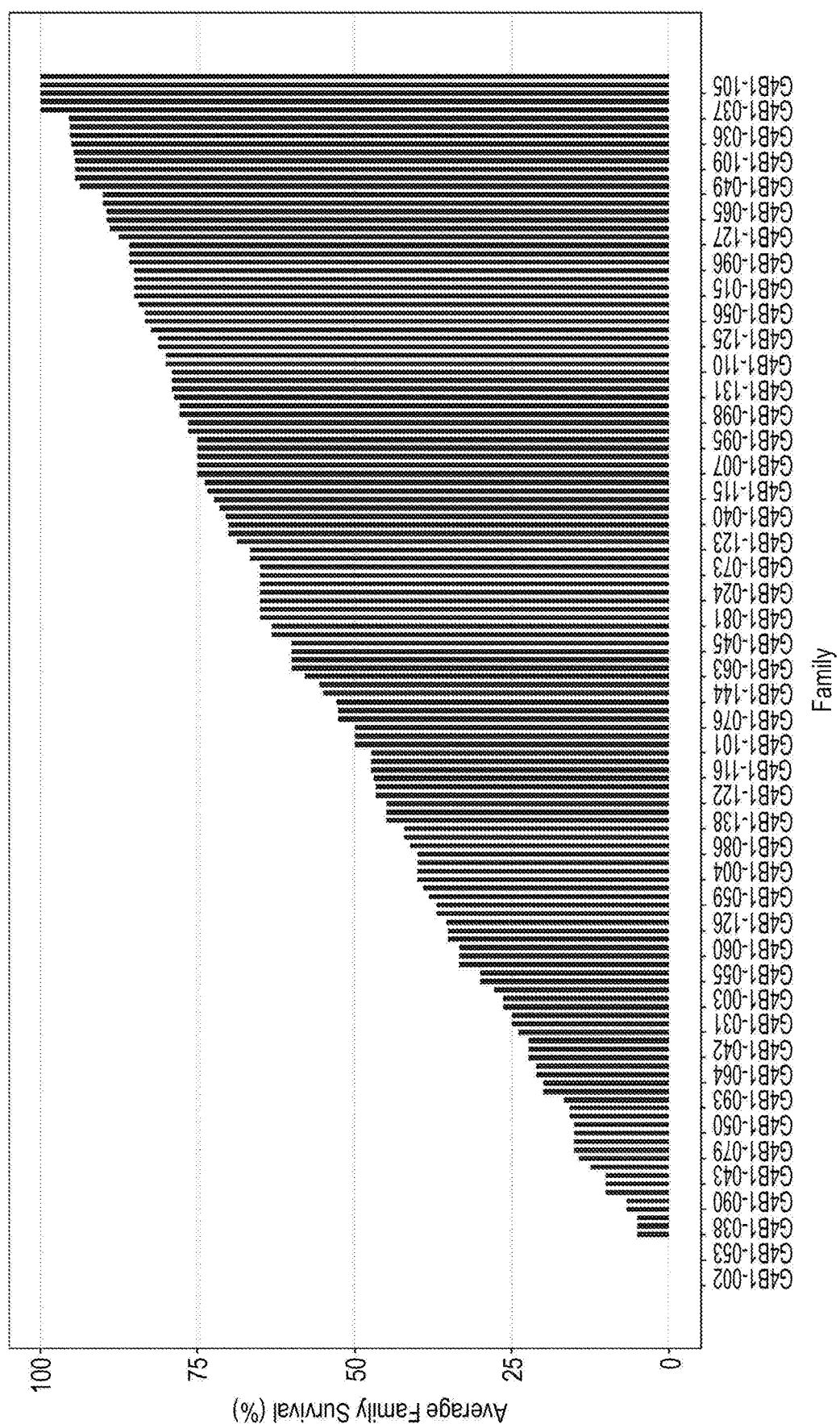
FIG. 2 shows the mean percentage survival rate mortality for each family rank ordered from low to high survival rate.

A high variation in mean survival rate for each family among the fish injected with S. iniae was observed, which ranges from 0% to 100%, with a coefficient of variation of 55% (FIG. 2).

The Pearson correlation between the mean family weight at the beginning of the challenge and S. iniae survival was negative but very low in magnitude (r=−0.10), suggesting that the variation in individual body weight had a marginal, if any, impact on survival during the trial.

Training Population

For each of the challenge tests a training population was constructed as a subsample of the fish sent to test. Families were clustered according to their genetic distances estimated from pedigree. From resulting clusters, half-sib families which maximize phenotypic variation were identified and within each family individuals were randomly sampled. After this process, 39 families were selected to create the training populations for S. iniae.

This population provided a total of 312 samples from a mean of 8.5 individuals per family, which exhibited a survival rate of 0.52±0.5 (mean f standard deviation).

Tissue samples were then transferred to deep 96 well plates, filled with 97% ethanol and genotyped.

Genotyping, Allele Call and Allele Filtering

Genotyping was performed using double digest restriction-site associated DNA sequencing (ddRADseq), a methodology where genome complexity is reduced by randomly cutting the DNA using restriction enzymes. The resulting fragments are then separated by their molecular weight and sequenced for posterior allele calling.

Allele calls were generated in VCF (Variant Call Format). For allele call, sequences were aligned to the tilapia genome assembly with GenBank assembly accession number GCA_001858045.2. In total, 83,752 SNPs were reported.

SNPs were then filtered for a minimum allele frequency (MAF) of 0.05, allele call and Hardy Weinberg equilibrium $p<1e^{-6}$. Two levels allele call were used to filter SNPs: 0.9 resulting in 16,440 SNPs after filtering. Data filtering was done using R statistical software.

Statistical Analysis

Statistical analysis was performed using ASReml V4.0 and R using the package NAM. The general fitted model was as follow:

$$y = \mu + Xb + Za + e$$

Where y is the vector of phenotypic records, $\mu$ is the overall mean, b is the unknown random allele substitution effect of the evaluated SNP, and a is the random additive genetic effect.

Significance of including each SNP was tested using a likelihood ratio test, which represents the improvement that each SNP provides to the model when not including the marker effect. Bonferroni corrected threshold was estimated at 5% significance.

Allele substitution effect was estimated as:

allele substitution=(effect of first homozygote−effect of the second homozygote)/2

Genetic variance explained by a SNP was estimated as $\sigma_{SNP}^2 = 2pga^2$, where p and q are allele frequencies, and a is the estimated allele substitution effect.

Markers

Figure 3:
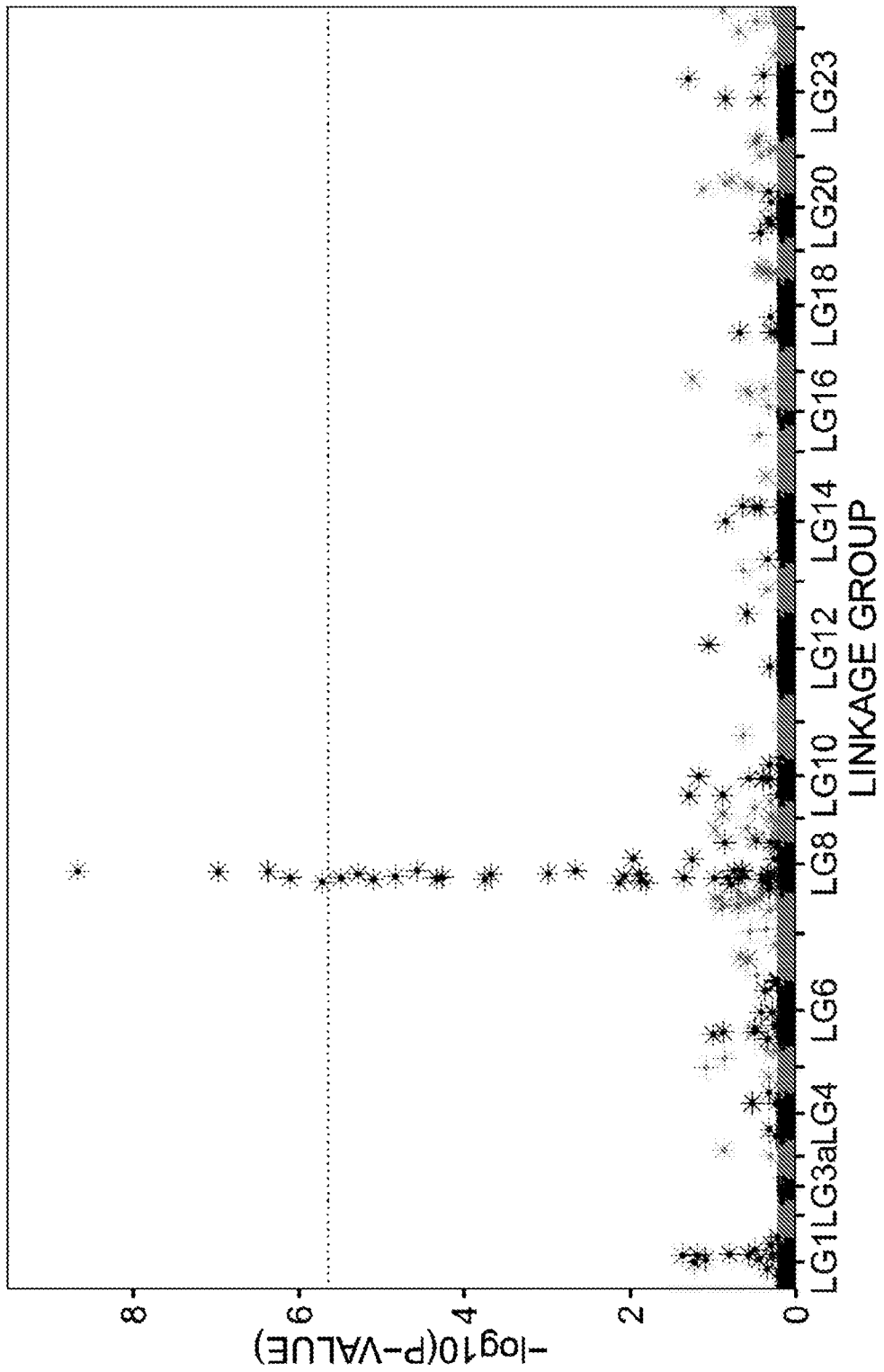
FIG. 3 shows the GWAS results for *S. iniae* using software ASReml V4.0 for model with SNP fitted as random effect, in which "Unknown" corresponds to markers in regions with unknown position on the genome.
Figure 4:
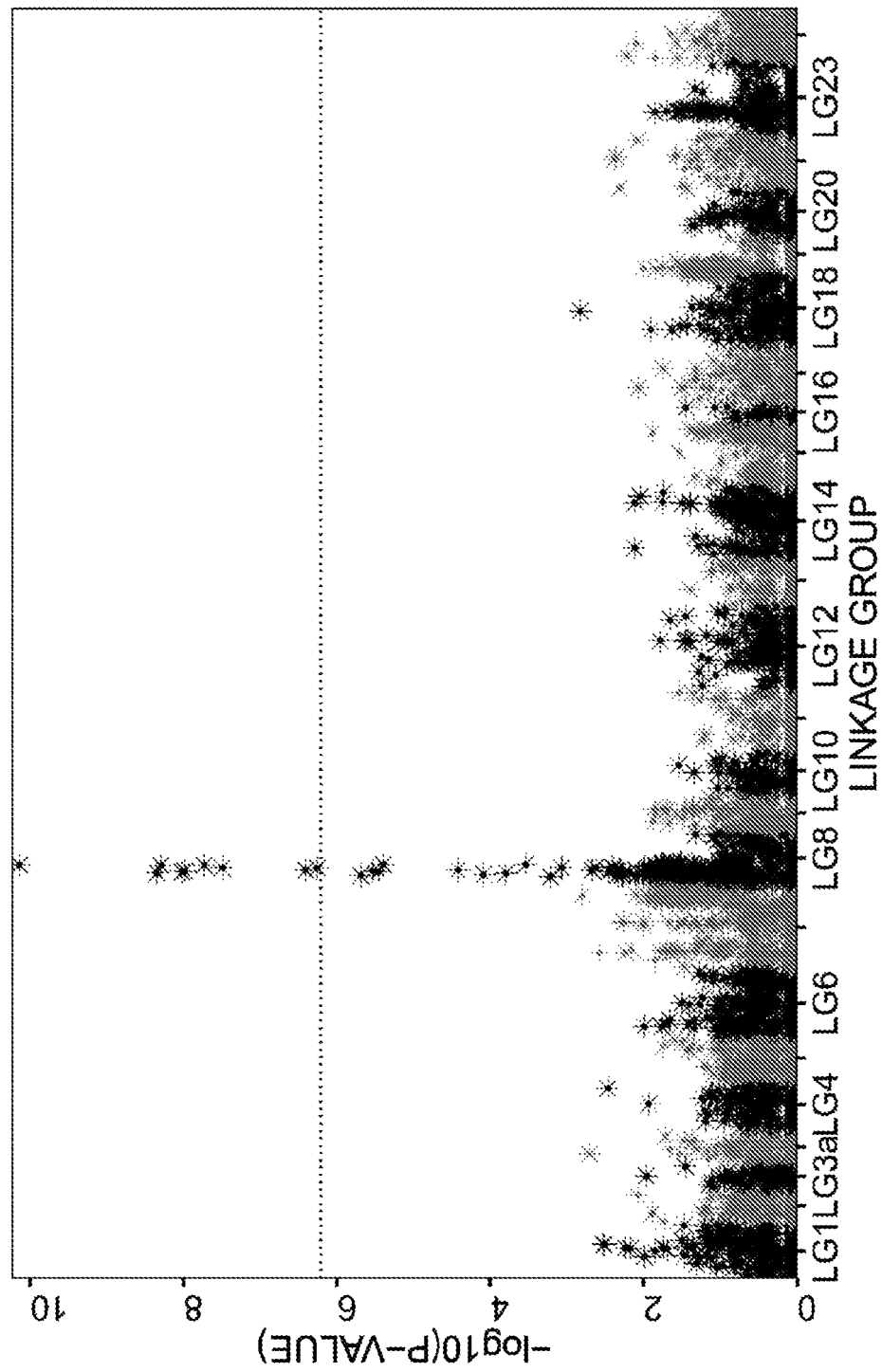
FIG. 4 shows the GWAS results for *S. iniae* using the package NAM implemented in R where SNP is fitted as random effect, in which "Unknown" corresponds to markers in regions with unknown position on the genome.

Genome-wide analysis results were summarized using Manhattan plots. FIG. 3 shows to results where SNP was fitted as random effect using the software ASReml, and FIG. 4 shows results for the model using the NAM package.

All models and software showed association in the same region in linkage group 8, and moreover, for the same markers.

A summary of results obtained using ASReml and NAM is shown in Tables 1 and 2, respectively. The numbers identifying each SNP (SNP id) consist of a prefix ("NC_031973.1") corresponding to the GenBank accession and version number for linkage group LG8 derived from genome assembly with GenBank assembly accession number GCA_001858045.2, and a suffix identifying the position of the SNP within NC_031973.1.

TABLE 1

Summary of results for markers using a model where SNP effect is fit as random effect using the software ASReml V4.1.

| SNP id | $\sigma_P^2$ | $\sigma_{SNP}^2$ | $\sigma_a^2$ | Substitution effect | Freq of p | Genetic variance of the SNP |
|---|---|---|---|---|---|---|
| NC_031973.1_5545222 | 0.284 | 0.193 | 0.055 | 0.211 | 0.151 | 0.054 |
| NC_031973.1_7142946 | 0.294 | 0.259 | 0.077 | 0.266 | 0.333 | 0.118 |
| NC_031973.1_9167743 | 0.292 | 0.234 | 0.068 | −0.229 | 0.167 | 0.064 |
| NC_031973.1_9209387 | 0.285 | 0.208 | 0.059 | −0.195 | 0.168 | 0.055 |
| NC_031973.1_9485417 | 0.297 | 0.271 | 0.080 | 0.276 | 0.333 | 0.123 |

TABLE 2

Summary of results for markers using of
a model where SNP effect
is fit as random
effect using the package NAM.

| SNP id | $\sigma^2_{SNP}$ | $h^2$ | Substitution effect | Frequency of p | Genetic variance of the SNP |
|---|---|---|---|---|---|
| NC_031973.1_6323968 | 0.054 | 0.195 | −0.320 | 0.198 | 0.102 |
| NC_031973.1_7142916 | 0.042 | 0.159 | 0.282 | 0.199 | 0.09 |
| NC_031973.1_7142946 | 0.029 | 0.114 | 0.232 | 0.333 | 0.103 |
| NC_031973.1_7497722 | 0.038 | 0.141 | 0.265 | 0.154 | 0.069 |
| NC_031973.1_7775443 | 0.034 | 0.13 | 0.252 | 0.182 | 0.075 |
| NC_031973.1_7782524 | 0.045 | 0.166 | −0.291 | 0.179 | 0.086 |
| NC_031973.1_9167743 | 0.051 | 0.185 | −0.311 | 0.167 | 0.086 |
| NC_031973.1_9209387 | 0.052 | 0.186 | −0.312 | 0.168 | 0.087 |
| NC_031973.1_9485417 | 0.041 | 0.159 | 0.279 | 0.333 | 0.124 |

An additional run of ASReml, where the five markers were fitted as random effects in the same model and random polygenic effect included, was used to obtain predicted phenotypes and correlations between predicted phenotypes and observed phenotypes. Pearson correlation value was 0.62 meaning that the five markers could predict the survival of fish with a high-medium reliability.

The locations and identity of the alleles for the markers are set out in Table 3.

TABLE 3

Allele locations and identity.

| SNP id | Chromosome | Position (bp) | Increased survival allele (R) | Decreased survival allele (S) |
|---|---|---|---|---|
| NC_031973.1_5545222 | 8 | 5545222 | A | G |
| NC_031973.1_6323968 | 8 | 6323968 | A | G |
| NC_031973.1_7142916 | 8 | 7142916 | A | G |
| NC_031973.1_7142946 | 8 | 7142946 | C | T |
| NC_031973.1_7497722 | 8 | 7497722 | T | C |
| NC_031973.1_7775443 | 8 | 7775443 | T | A |
| NC_031973.1_7782524 | 8 | 7782524 | C | T |
| NC_031973.1_9167743 | 8 | 9167743 | T | C |
| NC_031973.1_9209387 | 8 | 9209387 | G | A |
| NC_031973.1_9485417 | 8 | 9485417 | T | C |

Predictive Ability

The ability of markers to predict survival was assessed for sets obtained by ASReml and NAM separately. For both sets of markers total genotypic value ($\hat{G}$) was estimated for each family with both parents genotyped as:

$$\hat{G} = Wv$$

where W is a matrix with allele dosage with values 1 for heterozygotes and 0 or 2 for the first and second homozygote, and v is the vector of marker effects.

Figure 5:
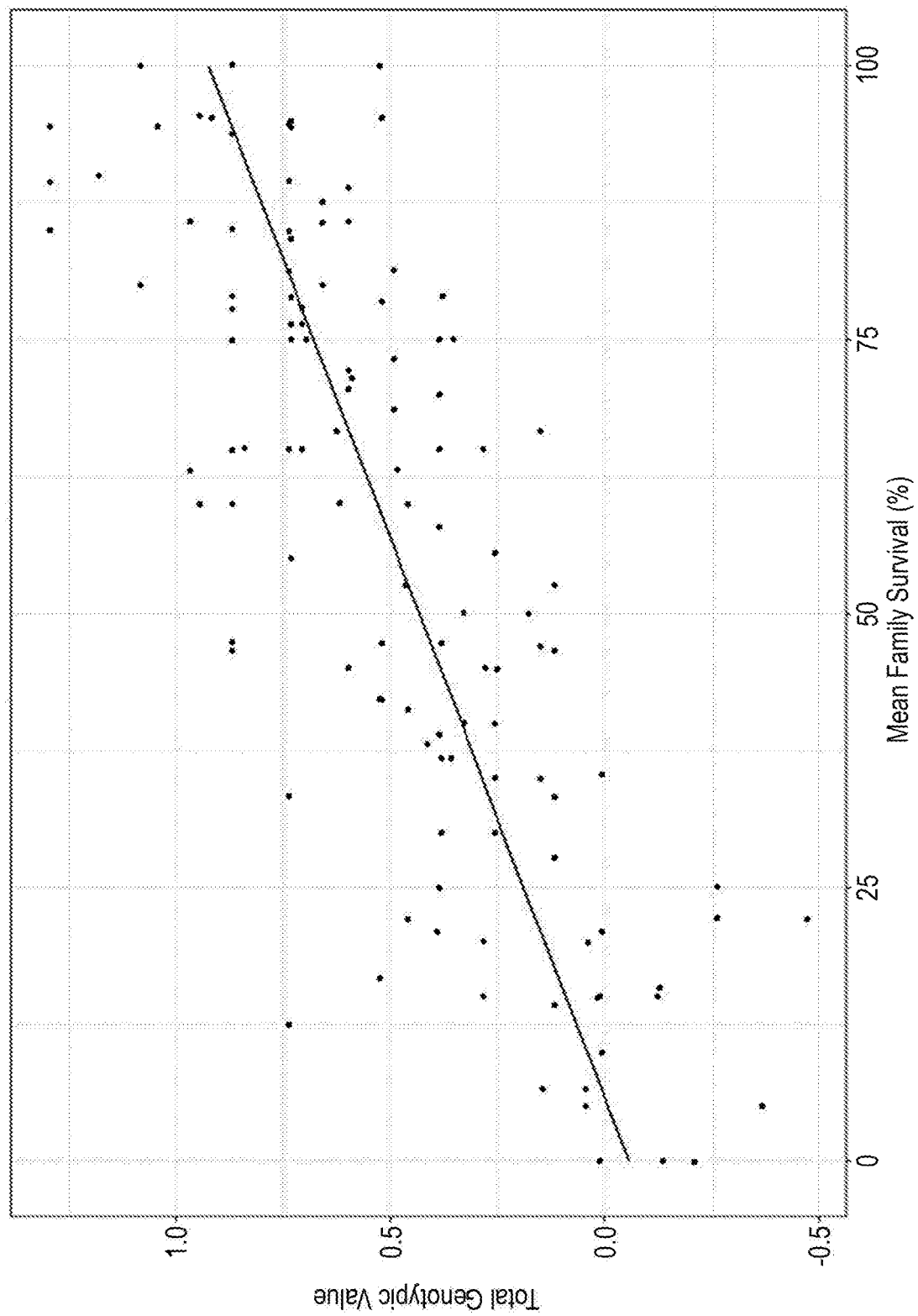
FIG. 5 shows the total genetic value plotted against the mean family survival for the markers tested by ASReml.
Figure 6:
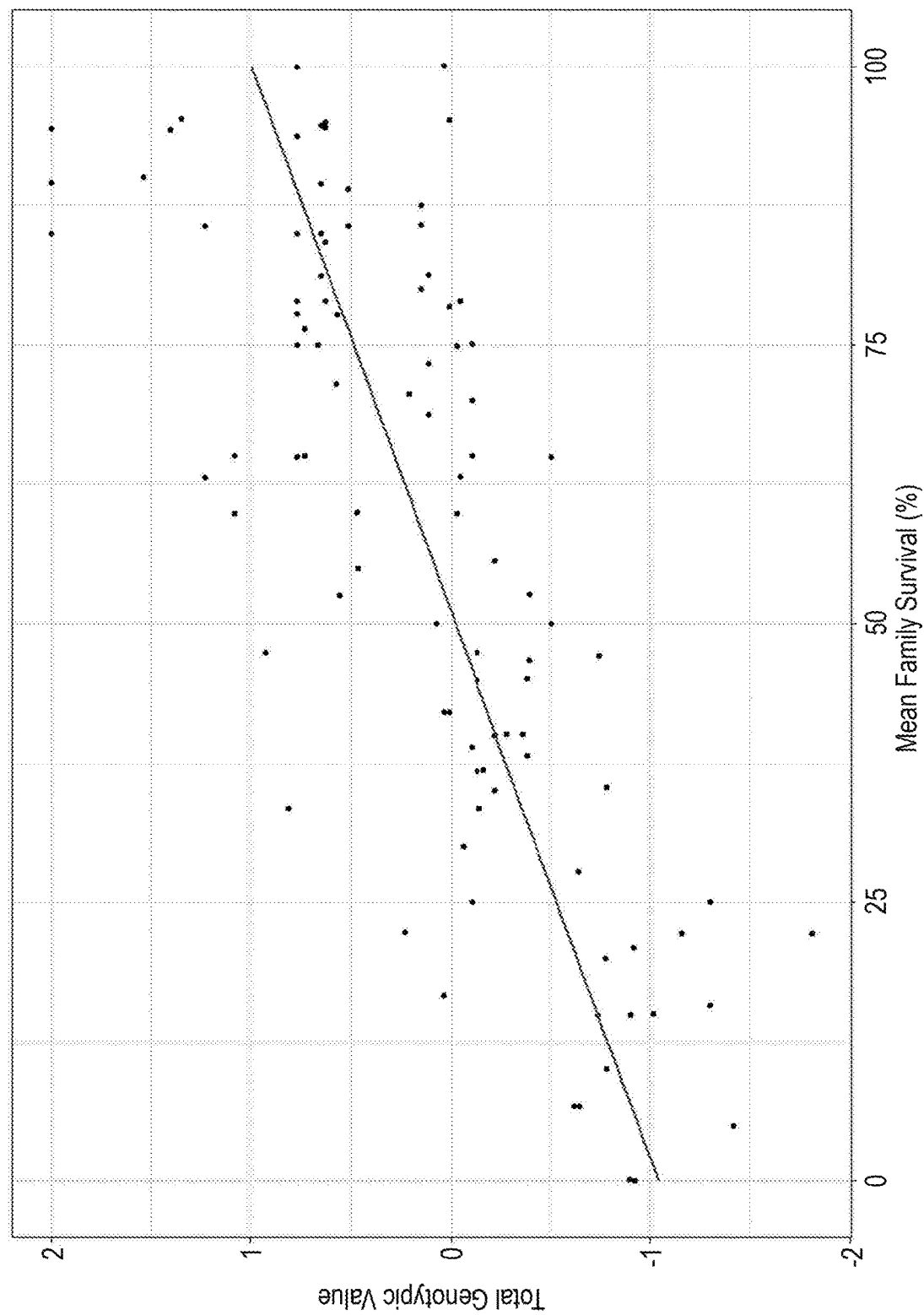
FIG. 6 shows the total genetic value plotted against the mean family survival for the markers tested by NAM.

The predictive ability of the markers was estimated as Pearson correlation of $\hat{G}$ and mean family survival. Predictive ability for the ASReml set of markers was 0.76 (FIG. 5) and for the NAM set of markers was 0.75 (FIG. 6).

For a family, the total genotypic value was estimated as the mean $\hat{G}$ value from both parents. Then the predictive ability of the markers was estimated as Pearson correlation of $\hat{G}$ and mean family survival.

Values were estimated for cases using one up to all markers of each set, including all possible combinations of SNPs and when either one or both progenitors were genotyped.

Relationship of the Haplotype Cross and Average Survival

The relationship between tilapia haplotypes and challenge test survival was assessed to demonstrate the feasibility of using SNP markers for selection of fish that are likely to survive *S. iniae* infection.

Haplotypes for nine SNPs were extracted and then related to mean family survival following *S. iniae* infection. Alleles were recoded as R and S for increased survival and reduced survival, respectively.

For each QTL found according to linkage disequilibrium, the mean average survival by haplotype of the crosses was determined (Tables 4 to 20). To simplify the reading of the data, when one of the breeders had a missing genotype, the cross was removed. For markers NC_031973.1_6323968, NC_031973.1_7782524, NC_031973.1_9167743 and NC_031973.1_9209387, at least one of the progenitors contributed an R allele and the mean survival of their families increased. Thus, these markers were designated to indicate survival following infection.

The contrary occurs with markers NC_031973.1_7142916, NC_031973.1_7142946, NC_031973.1_7497722, NC_031973.1_7775443 and NC_031973.1_9485417, in which crosses one of the progenitors contribute with at least one S allele, and the mean family survival is reduced. Thus, these markers were designated to indicate death following infection.

Sire-Dam Haplotype

For each candidate SNP/marker, mean average survival of the haplotype of one of the breeders at the time (sire or dam) was determined (Tables 4 to 20). A correlation of breeder haplotype and mean survival was observed.

TABLE 4

Survival by haplotype for SNP NC_031973.1_5545222.

| Sire | RR | | | | RS | | | |
|---|---|---|---|---|---|---|---|---|
| Dam | RR | RS | SS | Missing | RR | RS | SS | Missing |
| N | 81 | 26 | 1 | 4 | 11 | 5 | 1 | 3 |
| Mean | 65.14 | 34.17 | 50 | 49.08 | 57.2 | 34.86 | 22.22 | 35.98 |
| Min | 12.5 | 0 | 50 | 0 | 15 | 5 | 22.22 | 5 |
| Max | 100 | 77.78 | 50 | 100 | 95.24 | 52.63 | 22.22 | 52.94 |
| Q25 | 45 | 15 | 50 | 19.74 | 23.02 | 20 | 22.22 | 27.5 |
| Median | 70.59 | 34.17 | 50 | 48.16 | 71.43 | 46.67 | 22.22 | 50 |
| Q75 | 85 | 60.51 | 50 | 77.5 | 77.71 | 50 | 22.22 | 51.47 |

TABLE 5

Survival by haplotype for SNP NC_031973.1_5545222.

| Sire | SS | | Missing |
|---|---|---|---|
| Dam | RR | RS | RR |
| N | 3 | 1 | 7 |
| Mean | 15 | 0 | 43.14 |
| Min | 5 | 0 | 0 |
| Max | 33.33 | 0 | 90 |
| Q25 | 5.83 | 0 | 10 |
| Median | 6.67 | 0 | 26.32 |
| Q75 | 20 | 0 | 82.84 |

TABLE 6

Survival by haplotype for SNP NC_031973.1_6323968.

| Sire | RR | | RS | | | |
|---|---|---|---|---|---|---|
| Dam | SS | Missing | RR | RS | SS | Missing |
| N | 2 | 2 | 4 | 14 | 17 | 3 |
| Mean | 92.5 | 63.16 | 91.04 | 71.59 | 65.75 | 56.54 |
| Min | 85 | 26.32 | 85 | 33.33 | 22.22 | 50 |
| Max | 100 | 100 | 95.24 | 100 | 95 | 66.67 |
| Q25 | 88.75 | 44.74 | 88.36 | 55.26 | 52.63 | 51.47 |
| Median | 92.5 | 63.16 | 91.96 | 72.56 | 73.33 | 52.94 |
| Q75 | 96.25 | 81.58 | 94.64 | 88.93 | 81.25 | 59.8 |

TABLE 7

Survival by haplotype for SNP NC_031973.1_6323968.

| Sire | SS | | | | Missing | |
|---|---|---|---|---|---|---|
| Dam | RR | RS | SS | Missing | RS | SS |
| N | 1 | 21 | 49 | 13 | 4 | 7 |
| Mean | 76.47 | 74.72 | 39.81 | 30.34 | 56.21 | 47.08 |
| Min | 76.47 | 33.33 | 0 | 0 | 12.5 | 10 |
| Max | 76.47 | 100 | 100 | 76.47 | 83.33 | 90 |
| Q25 | 76.47 | 65 | 20 | 5 | 38.12 | 15.04 |
| Median | 76.47 | 75 | 36.84 | 21.05 | 64.51 | 41.18 |
| Q75 | 76.47 | 85 | 55 | 57.89 | 82.6 | 79.17 |

TABLE 8

Survival by haplotype for SNP NC_031973.1_7142916.

| Sire | RR | | | | RS | | | | Missing | |
|---|---|---|---|---|---|---|---|---|---|---|
| Dam | RR | RS | SS | Missing | RR | RS | SS | Missing | RR | RS |
| N | 71 | 23 | 1 | 7 | 17 | 10 | 2 | 3 | 7 | 2 |
| Mean | 67.41 | 38.88 | 0 | 45.25 | 49.89 | 29.01 | 23.61 | 35.98 | 55.05 | 7.89 |
| Min | 12.5 | 0 | 0 | 0 | 0 | 5 | 22.22 | 5 | 10 | 0 |
| Max | 100 | 77.78 | 0 | 95.45 | 95.24 | 52.63 | 25 | 52.94 | 90 | 15.79 |
| Q25 | 47.37 | 20 | 0 | 13.16 | 23.81 | 15.2 | 22.92 | 27.5 | 18.16 | 3.95 |
| Median | 75 | 36.84 | 0 | 40 | 60 | 25 | 23.61 | 50 | 82.35 | 7.89 |
| Q75 | 85.71 | 64.08 | 0 | 77.5 | 75 | 45 | 24.31 | 51.47 | 83.33 | 11.84 |

TABLE 9

Survival by haplotype for SNP NC_031973.1_7142946.

| Sire | RR | | | | RS | | | |
|---|---|---|---|---|---|---|---|---|
| Dam | RR | RS | SS | Missing | RR | RS | SS | Missing |
| N | 46 | 27 | 4 | 7 | 22 | 19 | 5 | 2 |
| Mean | 72.58 | 47.2 | 21.53 | 45.9 | 62.56 | 35.83 | 19.89 | 51.47 |
| Min | 30 | 0 | 0 | 0 | 0 | 5 | 15 | 50 |
| Max | 100 | 89.47 | 36.84 | 100 | 100 | 66.67 | 25 | 52.94 |
| Q25 | 60 | 21.64 | 10.71 | 13.16 | 48.22 | 24.42 | 15 | 50.74 |
| Median | 78.17 | 45 | 24.64 | 40 | 71.83 | 40 | 22.22 | 51.47 |
| Q75 | 88.98 | 67.79 | 35.46 | 77.5 | 80.67 | 48.53 | 22.22 | 52.21 |

TABLE 10

Survival by haplotype for SNP NC_031973.1_7142946.

| Sire | SS | | Missing | | |
|---|---|---|---|---|---|
| Dam | RS | NA | RR | RS | SS |
| N | 1 | 1 | 5 | 2 | 1 |
| Mean | 5 | 5 | 55.14 | 7.89 | 83.33 |
| Min | 5 | 5 | 10 | 0 | 83.33 |
| Max | 5 | 5 | 90 | 15.79 | 83.33 |
| Q25 | 5 | 5 | 10 | 3.95 | 83.33 |
| Median | 5 | 5 | 82.35 | 7.89 | 83.33 |
| Q75 | 5 | 5 | 83.33 | 11.84 | 83.33 |

TABLE 11

Survival by haplotype for SNP NC_031973.1_7497722.

| Sire | RR | | | RS | | | | Missing | |
|---|---|---|---|---|---|---|---|---|---|
| Dam | RR | RS | Missing | RR | RS | SS | Missing | RR | RS |
| N | 80 | 25 | 3 | 15 | 7 | 1 | 3 | 8 | 1 |
| Mean | 64.66 | 35.61 | 32.11 | 47.54 | 30.16 | 22.22 | 35.98 | 59.68 | 0 |
| Min | 0 | 0 | 0 | 0 | 5 | 22.22 | 5 | 10 | 0 |
| Max | 100 | 77.78 | 70 | 95.24 | 52.63 | 22.22 | 52.94 | 95.45 | 0 |
| Q25 | 45 | 15 | 13.16 | 18.61 | 17.89 | 22.22 | 27.5 | 22.24 | 0 |
| Median | 70.29 | 35.29 | 26.32 | 60 | 21.05 | 22.22 | 50 | 81.18 | 0 |
| Q75 | 85.18 | 50 | 48.16 | 75.74 | 48.33 | 22.22 | 51.47 | 85 | 0 |

TABLE 12

Survival by haplotype for SNP NC_031973.1_7775443.

| Sire | RR | | | | RS | | | | Missing | |
|---|---|---|---|---|---|---|---|---|---|---|
| Dam | RR | RS | SS | Missing | RR | RS | SS | Missing | RR | RS |
| N | 80 | 22 | 2 | 6 | 15 | 5 | 1 | 3 | 7 | 2 |
| Mean | 65.34 | 36.97 | 23.53 | 33.92 | 47.54 | 34.02 | 22.22 | 35.98 | 52.43 | 0 |
| Min | 12.5 | 0 | 0 | 0 | 0 | 5 | 22.22 | 5 | 10 | 0 |
| Max | 100 | 77.78 | 47.06 | 72.22 | 95.24 | 52.63 | 22.22 | 52.94 | 90 | 20 |
| Q25 | 45 | 16.25 | 11.76 | 6.58 | 18.61 | 15.79 | 22.22 | 27.5 | 18.16 | 5 |
| Median | 72.14 | 36.07 | 23.53 | 30.66 | 60 | 46.67 | 22.22 | 50 | 65 | 10 |
| Q75 | 85.71 | 59.87 | 35.29 | 61.25 | 75.74 | 50 | 22.22 | 51.47 | 82.84 | 15 |

TABLE 13

Survival by haplotype for SNP NC_031973.1_7782524.

| Sire | RR | | | RS | | | |
|---|---|---|---|---|---|---|---|
| Dam | RS | SS | Missing | RR | RS | SS | Missing |
| N | 1 | 4 | 1 | 4 | 14 | 20 | 7 |
| Mean | 85 | 74.82 | 26.32 | 91.04 | 76.55 | 66.68 | 51.47 |
| Min | 85 | 46.67 | 26.32 | 85 | 50 | 22.22 | 50 |
| Max | 85 | 100 | 26.32 | 95.24 | 100 | 95 | 52.94 |
| Q25 | 85 | 51.14 | 26.32 | 88.36 | 65 | 58.75 | 50.74 |
| Median | 85 | 76.32 | 26.32 | 91.96 | 75.73 | 71.96 | 51.47 |
| Q75 | 85 | 100 | 26.32 | 94.64 | 88.93 | 79.52 | 52.21 |

TABLE 14

Survival by haplotype for SNP NC_031973.1_7782524.

| Sire | SS | | | | Missing | |
|---|---|---|---|---|---|---|
| Dam | RR | RS | SS | Missing | RS | SS |
| N | 1 | 28 | 56 | 5 | 1 | 6 |
| Mean | 76.47 | 66.56 | 37.08 | 18 | 82.35 | 36.61 |
| Min | 76.47 | 12.5 | 0 | 0 | 82.35 | 0 |
| Max | 76.47 | 100 | 100 | 70 | 82.35 | 90 |
| Q25 | 76.47 | 47.19 | 16.45 | 0 | 82.35 | 10 |
| Median | 76.47 | 73.61 | 35 | 5 | 82.35 | 18.16 |
| Q75 | 76.47 | 83.75 | 48.03 | 15 | 82.35 | 69.08 |

TABLE 15

Survival by haplotype for SNP NC_031973.1_9167743.

| Sire | RR | | | RS | | | |
|---|---|---|---|---|---|---|---|
| Dam | RS | SS | Missing | RR | RS | SS | Missing |
| N | 1 | 2 | 1 | 4 | 10 | 20 | 2 |
| Mean | 85 | 100 | 26.32 | 91.04 | 77.77 | 64.7 | 51.47 |
| Min | 85 | 100 | 26.32 | 85 | 50 | 22.22 | 50 |
| Max | 85 | 100 | 26.32 | 95.24 | 100 | 95 | 52.94 |
| Q25 | 85 | 100 | 26.32 | 88.36 | 65 | 51.14 | 50.74 |
| Median | 85 | 100 | 26.32 | 91.96 | 78.89 | 68.63 | 51.47 |
| Q75 | 85 | 100 | 26.32 | 94.64 | 93.33 | 79.52 | 52.21 |

TABLE 16

Survival by haplotype for SNP NC_031973.1_9167743.

| Sire | SS | | | | Missing | |
|---|---|---|---|---|---|---|
| Dam | RR | RS | SS | Missing | RS | SS |
| N | 1 | 30 | 61 | 4 | 1 | 6 |
| Mean | 76.47 | 67.36 | 37.6 | 37.17 | 82.35 | 36.61 |
| Min | 76.47 | 12.5 | 0 | 0 | 82.35 | 0 |
| Max | 76.47 | 100 | 100 | 73.68 | 82.35 | 90 |
| Q25 | 76.47 | 48.68 | 15.79 | 3.75 | 82.35 | 10 |
| Median | 76.47 | 73.61 | 35 | 37.5 | 82.35 | 18.16 |
| Q75 | 76.47 | 84.58 | 55.56 | 70.92 | 82.35 | 69.08 |

TABLE 17

Survival by haplotype for SNP NC_031973.1_9209387.

| Sire | RR | | | RS | | | |
|---|---|---|---|---|---|---|---|
| Dam | RS | SS | Missing | RR | RS | SS | Missing |
| N | 3 | 1 | 2 | 4 | 12 | 21 | 3 |
| Mean | 89.81 | 100 | 63.16 | 91.04 | 73.93 | 66.65 | 45.42 |
| Min | 85 | 100 | 26.32 | 85 | 50 | 22.22 | 33.33 |
| Max | 94.44 | 100 | 100 | 95.24 | 100 | 95 | 52.94 |
| Q25 | 87.5 | 100 | 44.74 | 88.36 | 64.54 | 55 | 41.67 |
| Median | 90 | 100 | 63.16 | 91.96 | 72.56 | 70.59 | 50 |
| Q75 | 92.22 | 100 | 81.58 | 94.64 | 81.43 | 78.95 | 51.47 |

TABLE 18

Survival by haplotype for SNP NC_031973.1_9209387.

| Sire | SS | | | | Missing | |
|---|---|---|---|---|---|---|
| Dam | RR | RS | SS | Missing | RS | SS |
| N | 2 | 27 | 57 | 4 | 1 | 5 |
| Mean | 75.74 | 66.25 | 36.27 | 24.7 | 82.35 | 38.67 |
| Min | 75 | 12.5 | 0 | 0 | 82.35 | 0 |
| Max | 76.47 | 100 | 100 | 70 | 82.35 | 90 |
| Q25 | 75.37 | 47.02 | 15.79 | 3.75 | 82.35 | 10 |
| Median | 75.74 | 72.22 | 35 | 14.4 | 82.35 | 10 |
| Q75 | 76.1 | 84.17 | 47.37 | 35.36 | 82.35 | 83.33 |

TABLE 19

Survival by haplotype for SNP NC_031973.1_9485417.

| Sire | RR | | | | RS | | | |
|---|---|---|---|---|---|---|---|---|
| Dam | RR | RS | SS | Missing | RR | RS | SS | Missing |
| N | 36 | 33 | 6 | 3 | 28 | 13 | 5 | 4 |
| Mean | 73.71 | 59.6 | 31.84 | 22.11 | 58.15 | 29.26 | 21.71 | 44.49 |
| Min | 12.5 | 0 | 15.79 | 0 | 5 | 0 | 5 | 5 |
| Max | 100 | 100 | 45 | 40 | 95.24 | 52.63 | 35.29 | 70 |
| Q25 | 64.54 | 38.89 | 24.17 | 13.16 | 40 | 15 | 21.05 | 38.75 |
| Median | 82.29 | 65 | 33.42 | 26.32 | 64.38 | 27.78 | 22.22 | 51.47 |
| Q75 | 89.47 | 75 | 40.09 | 33.16 | 77.09 | 46.67 | 25 | 57.21 |

TABLE 20

Survival by haplotype for SNP NC_031973.1_9485417.

| Sire | SS | | | Missing | | |
|---|---|---|---|---|---|---|
| Dam | RR | RS | SS | RR | RS | SS |
| N | 3 | 4 | 1 | 4 | 2 | 1 |
| Mean | 56.11 | 12 | 0 | 48.33 | 54.33 | 0 |
| Min | 33.33 | 0 | 0 | 10 | 26.32 | 0 |
| Max | 75 | 22.22 | 0 | 90 | 82.35 | 0 |
| Q25 | 46.67 | 7.5 | 0 | 10 | 40.33 | 0 |
| Median | 60 | 12.89 | 0 | 46.67 | 54.33 | 0 |
| Q75 | 67.5 | 17.4 | 0 | 85 | 68.34 | 0 |

A wide range of values on the mean average survival was observed because crosses were not design according to their SNP genotypes. However, the RR haplotypes was always associated with a higher mean survival.

Analysing Multiple SNPs Increases Accuracy of Survival Prediction

The accuracy of survival prediction was quantified according the varied with sequencing strategy. The accuracy increased as the number of analysed SNPs increased (Tables 21 and 22). The accuracy also increased if both parents rather than one parent was genotyped (Table 21). Additionally, the accuracy if the dam progenitor rather than the sire progenitor was genotyped (Table 22).

TABLE 21

Summary of predictive ability when both or one progenitor were genotyped using different numbers of SNPs.

| Progenitor genotyped | Method for estimate marker effects | Number of SNPs included | Predictive accuracy | | |
|---|---|---|---|---|---|
| | | | Mean | MM | Max |
| Both parents genotyped | ASReml | 1 | 0.572 | 0.481 | 0.606 |
| | | 2 | 0.674 | 0.600 | 0.720 |
| | | 3 | 0.717 | 0.679 | 0.751 |
| | | 4 | 0.744 | 0.733 | 0.756 |
| | | 5 | 0.763 | 0.763 | 0.763 |
| | NAM | 1 | 0.547 | 0.437 | 0.606 |
| | | 2 | 0.643 | 0.438 | 0.725 |
| | | 3 | 0.679 | 0.485 | 0.758 |
| | | 4 | 0.700 | 0.547 | 0.758 |
| | | 5 | 0.714 | 0.603 | 0.763 |
| | | 6 | 0.725 | 0.662 | 0.760 |
| | | 7 | 0.733 | 0.694 | 0.758 |

TABLE 21-continued

Summary of predictive ability when both or one progenitor were genotyped using different numbers of SNPs.

| Progenitor genotyped | Method for estimate marker effects | Number of SNPs included | Predictive accuracy Mean | MM | Max |
|---|---|---|---|---|---|
| | | 8 | 0.741 | 0.719 | 0.754 |
| | | 9 | 0.748 | 0.748 | 0.748 |
| One of the parents (sire or dam) | ASReml | 1 | 0.400 | 0.333 | 0.445 |
| | | 2 | 0.481 | 0.430 | 0.520 |
| | | 3 | 0.516 | 0.477 | 0.543 |
| | | 4 | 0.538 | 0.531 | 0.549 |
| | | 5 | 0.553 | 0.553 | 0.553 |
| | NAM | 1 | 0.392 | 0.314 | 0.445 |
| | | 2 | 0.466 | 0.323 | 0.532 |
| | | 3 | 0.497 | 0.359 | 0.557 |
| | | 4 | 0.514 | 0.402 | 0.559 |
| | | 5 | 0.526 | 0.437 | 0.573 |
| | | 6 | 0.535 | 0.492 | 0.570 |
| | | 7 | 0.542 | 0.520 | 0.565 |
| | | 8 | 0.548 | 0.537 | 0.561 |
| | | 9 | 0.553 | 0.553 | 0.553 |

TABLE 22

Summary of predictive ability when either sire or dam were genotyped using different numbers of SNPs.

| Progenitor genotyped | Method for estimate marker effects | Number of SNPs included | Predictive accuracy Mean | Min | Max |
|---|---|---|---|---|---|
| Sire | ASReml | 1 | 0.340 | 0.269 | 0.426 |
| | | 2 | 0.414 | 0.313 | 0.479 |
| | | 3 | 0.446 | 0.380 | 0.481 |
| | | 4 | 0.467 | 0.446 | 0.494 |
| | | 5 | 0.482 | 0.482 | 0.482 |
| | NAM | 1 | 0.321 | 0.198 | 0.426 |
| | | 2 | 0.398 | 0.215 | 0.492 |
| | | 3 | 0.429 | 0.250 | 0.487 |
| | | 4 | 0.446 | 0.275 | 0.502 |
| | | 5 | 0.458 | 0.329 | 0.499 |
| | | 6 | 0.467 | 0.397 | 0.498 |
| | | 7 | 0.473 | 0.443 | 0.498 |
| | | 8 | 0.478 | 0.463 | 0.492 |
| | | 9 | 0.482 | 0.482 | 0.482 |
| Dam | ASReml | 1 | 0.457 | 0.399 | 0.524 |
| | | 2 | 0.544 | 0.464 | 0.613 |
| | | 3 | 0.584 | 0.533 | 0.626 |
| | | 4 | 0.608 | 0.570 | 0.621 |
| | | 5 | 0.622 | 0.622 | 0.622 |
| | NAM | 1 | 0.456 | 0.412 | 0.524 |
| | | 2 | 0.531 | 0.418 | 0.616 |
| | | 3 | 0.562 | 0.454 | 0.658 |
| | | 4 | 0.581 | 0.468 | 0.656 |
| | | 5 | 0.595 | 0.517 | 0.654 |
| | | 6 | 0.605 | 0.551 | 0.659 |
| | | 7 | 0.614 | 0.580 | 0.654 |
| | | 8 | 0.622 | 0.602 | 0.644 |
| | | 9 | 0.628 | 0.628 | 0.628 |

Sequence Listing of Alleles Indicating Increased Survival and Decreased Survival The sequences of the alleles indicating increased survival and decreased survival for each SNP with flanking regions are shown below. The residue showing the survival allele is highlighted in bold between square brackets. The length of the flanking regions around the alleles shown below is arbitrary. The nucleic acid of the allele and its position within the linkage group defines the SNP. If required, longer flanking regions may be determined by standard sequence analysis methods from the full sequence of the linkage group as defined by the sequence with GenBank accession no. NC_031973.1.

```
NC_031973.1_7142946 increased survival allele [SEQ ID NO: 1]:
AGCAAATCGCATGTGTGAGCCAGCCCGAAGTCACAGGAGCTGTCCTTGGTGCTGAGAGGGAG

GCAGCTGTYCGAGTGTTTTCCTGAACAGACCTGAAGCC[C]GCTGGAYTTTGTTTCTTTCCT

TCAGCTAATCCTTTCCATGCAGCCTGCATCAGGATGTCAATTCATAATAAAAAGTATACAGG

CACCAAGCAGTCAATCA

NC_031973.1_7142946 decreased survival allele [SEQ ID NO: 2]:
AGCAAATCGCATGTGTGAGCCAGCCCGAAGTCACAGGAGCTGTCCTTGGTGCTGAGAGGGAG

GCAGCTGTYCGAGTGTTTTCCTGAACAGACCTGAAGCC[T]GCTGGAYTTTGTTTCTTTCCT

TCAGCTAATCCTTTCCATGCAGCCTGCATCAGGATGTCAATTCATAATAAAAAGTATACAGG

CACCAAGCAGTCAATCA

NC_031973.1_7775443 increased survival allele [SEQ ID NO: 3]:
TGTCTGACAGTCCTTATTCAGCACTGATGATGGAGGCCTAYCAGAGGCCAGCATTTCGGGCT

CCTGCTAACATTACAAAATAAAATACCAGCTCGTATGT[T]TGACTTACTGAAACCTGCATG

TCCTCTCACGGCYCAGTGCTGGTCGGCAGCGCCYGGGGGTGAAGCGATGTCACGACYCYGTG

CACGTTTACATCATCGT

NC_031973.1_7775443 decreased survival allele [SEQ ID NO: 4]:
TGTCTGACAGTCCTTATTCAGCACTGATGATGGAGGCCTAYCAGAGGCCAGCATTTCGGGCT

CCTGCTAACATTACAAAATAAAATACCAGCTCGTATGT[A]TGACTTACTGAAACCTGCATG
```

-continued

TCCTCTCACGGCYCAGTGCTGGTCGGCAGCGCCYGGGGGTGAAGCGATGTCACGACYCYGTG

CACGTTTACATCATCGT

NC_031973.1_6323968 increased survival allele [SEQ ID NO: 5]:
TTTTTTGCTCTGTGTGGTGGTTTTATGGCTTCTTCACACTAACATGGTTCTTATGTAAATAG

TTCCTGAGATGTTYGTCCTGGAGGAGCAGCACAGTGCA[A]ATCTCCACGCTGTAAGCCTGA

ACAAACTGATGCTTGTTCAGCCCTTTGATGCTGAAGGCAAATTAAAGAGCGCTGGCTCTCCA

CGCYTCCTCTGGTATAA

NC_031973.1_6323968 decreased survival allele [SEQ ID NO: 6]:
TTTTTTGCTCTGTGTGGTGGTTTTATGGCTTCTTCACACTAACATGGTTCTTATGTAAATAG

TTCCTGAGATGTTYGTCCTGGAGGAGCAGCACAGTGCA[G]ATCTCCACGCTGTAAGCCTGA

ACAAACTGATGCTTGTTCAGCCCTTTGATGCTGAAGGCAAATTAAAGAGCGCTGGCTCTCCA

CGCYTCCTCTGGTATAA

NC_031973.1_7142916 increased survival allele [SEQ ID NO: 7]:
CACTCTGGTGGATGTTGAGAAGCTAATGTGAGCAAATCGCATGTGTGAGCCAGCCCGAAGTC

ACAGGAGCTGTCCTTGGTGCTGAGAGGGAGGCAGCTGT[A]CGAGTGTTTTCCTGAACAGAC

CTGAAGCCYGCTGGAYTTTGTTTCTTTCCTTCAGCTAATCCTTTCCATGCAGCCTGCATCAG

GATGTCAATTCATAATA

NC_031973.1_7142916 decreased survival allele [SEQ ID NO: 8]:
CACTCTGGTGGATGTTGAGAAGCTAATGTGAGCAAATCGCATGTGTGAGCCAGCCCGAAGTC

ACAGGAGCTGTCCTTGGTGCTGAGAGGGAGGCAGCTGT[G]CGAGTGTTTTCCTGAACAGAC

CTGAAGCCYGCTGGAYTTTGTTTCTTTCCTTCAGCTAATCCTTTCCATGCAGCCTGCATCAG

GATGTCAATTCATAATA

NC_031973.1_7497722 increased survival allele [SEQ ID NO: 9]:
GCATATGCAGAATYAAAGAACCATYGAGCTGTGATTTGACAAAGGAAGCTGCGAGAGTGTGC

AGCGCTTTCATTGAAAAGCTAAAACACAAAATCCATTT[T]ATGGGGTTAAAAATGGGATTG

GGCAGGTGGGYGACTCACCTGTCTTCTTGGTGGAAAGCCTATAAGATCAGCTGACCTGCTCA

TTGCTGTGTCTCTGACG

NC_031973.1_7497722 decreased survival allele [SEQ ID NO: 10]:
GCATATGCAGAATYAAAGAACCATYGAGCTGTGATTTGACAAAGGAAGCTGCGAGAGTGTGC

AGCGCTTTCATTGAAAAGCTAAAACACAAAATCCATTT[C]ATGGGGTTAAAAATGGGATTG

GGCAGGTGGGYGACTCACCTGTCTTCTTGGTGGAAAGCCTATAAGATCAGCTGACCTGCTCA

TTGCTGTGTCTCTGACG

NC_031973.1_9167743 increased survival allele [SEQ ID NO: 11]:
GCTCTGGAAAGTGACTTAACATCAGAGTGTGCTGATCYTGTGTGCGTTTGTGTAAACTGTGG

GAGCAGGAAGCAGTCAGCACCTCTTCAAAGTAAGAGTC[T]AGTGTTTGCGCTGCTCTGATT

TTAGCGGCTGGACTGGAAGAATCGTCCCGTCTGCACGGGTTGACCTTCTGTGATCTGTGATC

AGAACTTCGGAGTTACT

NC_031973.1_9167743 decreased survival allele [SEQ ID NO: 12]:
GCTCTGGAAAGTGACTTAACATCAGAGTGTGCTGATCYTGTGTGCGTTTGTGTAAACTGTGG

GAGCAGGAAGCAGTCAGCACCTCTTCAAAGTAAGAGTC[C]AGTGTTTGCGCTGCTCTGATT

TTAGCGGCTGGACTGGAAGAATCGTCCCGTCTGCACGGGTTGACCTTCTGTGATCTGTGATC

AGAACTTCGGAGTTACT

NC_031973.1_7782524 increased survival allele [SEQ ID NO: 13]:
CCCTTTTTAATGCCTCACTTTTCTCTGATTGYCCTCCTCTGACAYACAGAAGGTTTCAGCAG

CAGCTGGCTGTAGTTTCTCYGCTCACACCTGAGCTTTG[C]GGTCAGATGACCAYGTCAGGG

-continued

TYTCTCYGTGACATCACACATATCCGTGTCTGTGCTGCCCTGGAGATCTGCCGTACCTGATG

ATGGGAACCTCTAAGAA

NC_031973.1_7782524 decreased survival allele [SEQ ID NO: 14]:
CCCTTTTTAATGCCTCACTTTTCTCTGATTGYCCTCCTCTGACAYACAGAAGGTTTCAGCAG

CAGCTGGCTGTAGTTTCTCYGCTCACACCTGAGCTTTG[T]GGTCAGATGACCAYGTCAGGG

TYTCTCYGTGACATCACACATATCCGTGTCTGTGCTGCCCTGGAGATCTGCCGTACCTGATG

ATGGGAACCTCTAAGAA

NC_031973.1_9209387 increased survival allele [SEQ ID NO: 15]:
AGACATTCCCTACAGATCTGCAAACTTGGATTACTTCGAGTATTCATCAGTCGCCCAACAAC

AGAAACTGAATAGAAAACAGCTGGAACACCTGGATGTA[G]GAGTGCTGTGACACAACTTCA

GATTTTAACTGTGAGCTCAGTTTACTGAATTACTGAACAACTTATACATCATCCTCATCACC

ACCATCATCATCATCCT

NC_031973.1_9209387 decreased survival allele [SEQ ID NO: 16]:
AGACATTCCCTACAGATCTGCAAACTTGGATTACTTCGAGTATTCATCAGTCGCCCAACAAC

AGAAACTGAATAGAAAACAGCTGGAACACCTGGATGTA[A]GAGTGCTGTGACACAACTTCA

GATTTTAACTGTGAGCTCAGTTTACTGAATTACTGAACAACTTATACATCATCCTCATCACC

ACCATCATCATCATCCT

NC_031973.1_9485417 increased survival allele [SEQ ID NO: 17]:
AATGCACYTGACCTCTGAACACTCACAGAAATCTAAAAACGAGYCATCTGATGTAAACTGAC

CTGAAGACTGAAGAGAAGAAGACAGGAGGAAGTAAAGC[T]GTYAAGAAGCAGTGCCTGCAG

CTGGAGCACCACCACCAYCCACACYCACTGCCATGGAAACAACCGCGGGTAGTTTCCATGGC

AGAGTGTCACTGACTAT

NC_031973.1_9485417 decreased survival allele [SEQ ID NO: 18]:
AATGCACYTGACCTCTGAACACTCACAGAAATCTAAAAACGAGYCATCTGATGTAAACTGAC

CTGAAGACTGAAGAGAAGAAGACAGGAGGAAGTAAAGC[C]GTYAAGAAGCAGTGCCTGCAG

CTGGAGCACCACCACCAYCCACACYCACTGCCATGGAAACAACCGCGGGTAGTTTCCATGGC

AGAGTGTCACTGACTAT

NC_031973.1_5545222 increased survival allele [SEQ ID NO: 19]:
TATCGGTCTCATCCAGCCTGGGACTGGGTTAGGTCACCTAGAAGGAACTGGAAAGAACCACT

ACTCTGCTTAGCCTGCTGCCACCACAACCCAACCGCAG[A]GGGAACATGGTGATGCTCTTA

TTTCTCCCTTCTGTTATTCTCAGAGGGAACCACTCACACTTTCTGCTGCTGGCAGACATCTG

CTCATCACTGGGCTGAA

NC_031973.1_5545222 decreased survival allele [SEQ ID NO: 20]:
TATCGGTCTCATCCAGCCTGGGACTGGGTTAGGTCACCTAGAAGGAACTGGAAAGAACCACT

ACTCTGCTTAGCCTGCTGCCACCACAACCCAACCGCAG[C]GGGAACATGGTGATGCTCTTA

TTTCTCCCTTCTGTTATTCTCAGAGGGAACCACTCACACTTTCTGCTGCTGGCAGACATCTG

CTCATCACTGGGCTGAA

The background technology as set out in the following publications was used in the development and enablement of the present invention:

Statistical Methods for QTL Detection and Software Used

Fernando, R. and Grossman, M. (1989) 'Marker assisted selection using best linear unbiased prediction', Genetics, selection, evolution: GSE, 21(4), pp. 467-477.

Gilmour, A. R. (2007) 'Mixed model regression mapping for QTL detection in experimental crosses', Computational Statistics & Data Analysis. North-Holland, 51(8), pp. 3749-3764.

Massault, C., Bovenhuis, H., Haley, C. and de Koning, D. J. (2008) 'QTL mapping designs for aquaculture', Aquaculture. Elsevier B. V., 285(1-4), pp. 23-29.

Goddard, M. E. and Hayes, B. J. (2009) 'Mapping genes for complex traits in domestic animals and their use in breeding programmes.', Nature reviews. Genetics. Nature Publishing Group, 10(6), pp. 381-91.

Xavier, A., Xu, S., Muir, W. M. and Rainey, K. M. (2015) 'NAM: association studies in multiple populations: FIG. 1.', Bioinformatics, 31(23), p. btv448.

Methods in Molecular Biology

Baird, N. A., Etter, P. D., Atwood, T. S., Currey, M. C., Shiver, A. L., Lewis, Z. A., Selker, E. U., Cresko, W. A. and Johnson, E. A. (2008) 'Rapid SNP Discovery and Genetic Mapping Using Sequenced RAD Markers', PLoS ONE. Edited by J. C. Fay. Public Library of Science, 3(10), p. e3376.

Peterson, B. K., Weber, J. N., Kay. E. H., Fisher, H. S. and Hoekstra. H. E. (2012) 'Double Digest RADseq: An Inexpensive Method for De Novo SNP Discovery and Genotyping in Model and Non-Model Species', PLoS ONE. Edited by L. Orlando. Public Library of Science, 7(5), p. e37135.

Reed, E., Nunez, S., Kulp, D., Qian, J., Reilly, M. P. and Foulkes, A. S. (2015) 'A guide to genome-wide association analysis and post-analytic interrogation', Statistics in Medicine, 34(28), pp. 3769-3792.

Tilapia Genome

Conte, M. A., Gammerdinger, W. J., Bartie, K. L., Penman, D. J. and Kocher, T. D. (2017) 'A high quality assembly of the Nile Tilapia (Oreochromis niloticus) genome reveals the structure of two sex determination regions'. BMC Genomics. BioMed Central, 18(1), p. 341.

EXAMPLE 2—SELECTING BROODSTOCK USING SNP MARKERS FOR A DISEASE RESISTANCE QTL

Using the methods described herein. SNPs and combinations of SNPs, i.e. haplotypes, have been assigned breeding values for the survivability to *Streptococcus iniae* infection. The breeding value can be qualitative, i.e. increased survival or decreased survival, or quantitative, i.e. a numerical breeding value for the predicted survival of progeny to *Streptococcus iniae* infection. Each animal carries two haplotypes and two variants of the QTL. Each animal would be ascribed a breeding value as qualitative genotype, i.e. (i) increased survival:increased survival; (ii) increased survival:decreased survival; or (iii) decreased survival:decreased survival. Alternatively, each animal is ascribed the average breeding value of the two haplotypes carried by the individual.

Breeding candidates are genotyped for the SNPs to determine the variants and haplotypes that they carry, and individual breeding values are determined based on their haplotypes.

Individual males and females with the genotypes associated with the higher survivability or breeding values would be selected as broodstock. The males and females were mated according to good custom and practice of pedigree breeding programmes for the species. The resulting offspring are predicted to have improved pathogen resistance compared to the average disease resistance of the previous generation.

The invention claimed is:

1. A method of producing a tilapia offspring resistant to *Streptococcus iniae* infection, the method comprising the steps of:
    a) obtaining a tissue sample from a tilapia;
    b) detecting in the sample from the tilapia the presence of alleles conferring resistance to infection by *Streptococcus iniae* at one or more DNA polymorphism selected from the group consisting of: NC_031973.1_7142946, NC_031973.1_9167743, NC_031973.1_6323968, NC_031973.1_7142916, NC_031973.1_7497722, NC_031973.1_7775443, NC_031973.1_7782524, NC_031973.1_9209387, NC_031973.1_9485417, and NC_031973.1_5545222;
    c) selecting tilapia having alleles conferring resistance to infection by *Streptococcus iniae* from step b, wherein the alleles having resistance are selected from the group consisting of SEQ ID NOs: 1; 3; 5; 7; 9; 11; 13; 15; 17; and 19; and
    d) subjecting the selected tilapia to aquaculture to produce tilapia offspring comprising resistance to infection by *Streptococcus iniae*.

2. The method according to claim 1, wherein the alleles in the sample are analysed by nucleotide sequencing.

3. The method according to claim 1, wherein the method comprises determining the alleles present at two or more DNA polymorphism in the tilapia.

4. The method of claim 1, further comprising using the tilapia offspring to form a broodstock.

5. The method of claim 1, further comprising using the tilapia offspring to produce tilapia eggs.

6. The method according to claim 1, wherein the tilapia is a Nile tilapia.

7. The method according to claim 3, wherein the method comprises determining the alleles present at NC 031973.1 9209387 and NC 031973.1 9485417.

* * * * *